United States Patent [19]
Brill

[11] Patent Number: 5,639,867
[45] Date of Patent: Jun. 17, 1997

[54] TTTR AS PROTECTIVE GROUP IN NUCLEOTIDE SYNTHESIS

[75] Inventor: Wolfgang K.-D. Brill, Schopfheim, Germany

[73] Assignee: Ciba Geigy Corporation, Tarrytown, N.Y.

[21] Appl. No.: 304,456

[22] Filed: Sep. 12, 1994

[30] Foreign Application Priority Data

Sep. 17, 1993 [CH] Switzerland ............................ 2813/93

[51] Int. Cl.$^6$ ...................................................... C07H 1/00
[52] U.S. Cl. .................... 536/22.1; 536/25.3; 536/25.31; 536/25.33; 536/25.34; 536/26.7; 536/26.71; 536/26.72; 536/26.74; 536/26.8; 536/27.11; 536/27.6; 536/28.1; 536/28.5; 536/28.51; 536/28.52; 536/28.53; 536/28.54; 536/28.55
[58] Field of Search ......................... 536/25.3, 25.31, 536/25.33, 25.34, 26.7, 26.71, 26.72, 26.74, 26.8, 27.11, 27.6, 28.1, 28.5, 28.51, 28.52, 28.53, 28.54, 28.55

[56] References Cited

U.S. PATENT DOCUMENTS 5,268,464 12/1993 Brill .

OTHER PUBLICATIONS

S.L. Beaucage et al., Tetrahedron, 48, pp. 2223–2311 (1992).
Gibson, H.W., et al., J. Org. Chem. 58, pp. 3748–3756 (1993).
Takenaka, S. et al. Analytical Sciences Feb. 1992 vol. 8 pp. 3–7.
Townsend, L., Chemistry of Nucleosides and Nucleotides, vol. 1 (1988) pp. 283–367 Chapter 3.
Gait, M.J. et al Chemical and Enzymatic Synthesis of Gene Fragments, Verlag Chemie, Weinheim, 1–42 (1982).
Ashton, P. et al, J. Chem. Soc., Chem. Commun. pp. 1124–1128 (1992).
Marvel, C.S. et al. J. Am. Chem. Soc. 63:1892–1896 (1941) vol. 63.

Primary Examiner—James O. Wilson
Attorney, Agent, or Firm—Marla J. Mathias; Gregory D. Ferraro; George R. Dohmann

[57] ABSTRACT

The invention relates to nucleosides, nucleotides and oligonucleotides carrying in their basic structure a primary hydroxyl group protected by tris-4,4',4"-tert-butylphenylmethyl, to processes for the preparation of said nucleosides and nucleotides, to a process for the preparation of oligonucleotides, and to the use of said protected nucleosides, nucleotides and oligonucleotides.

12 Claims, No Drawings

TTTR AS PROTECTIVE GROUP IN NUCLEOTIDE SYNTHESIS

The present invention relates to nucleosides, nucleotides and oligonucleotides carrying in their basic structure a primary hydroxyl group protected by tris-4,4',4"-tert-butylphenylmethyl, to processes for the preparation of said nucleosides and nucleotides, to a process for the preparation of oligonucleotides, and to the use of said protected nucleosides, nucleotides and oligonucleotides.

Before the synthesis of oligonucleotides which, on account of their ability to interact with nucleic acids (i.a. antisense oligonucleotides) and of the biological activity associated therewith, have met with wide interest, the nucleosides and nucleoside analogs employed are provided with protective groups at their 5'-positions. These groups are typically phenylxanthen-9-yl (pixyl) and trityl protective groups [Beaucage, S. L., Iyer, R., Tetrahedron 48:2223–2311 (1992)]. In the case of the pixyl as well as the di-p-anisylphenylmethyl (DMTr) and the p-anisyldiphenylmethyl (MMTr) group, the poor regioselectivity results in yield losses even in the introduction of these groups. A further drawback of these trityl groups with long O-alkyl chains is that, although the chromatographic purification of the oligonucleotides formed from them is made easier, the nucleoside monomers protected by said groups have only a minor tendency to form solids or crystalline solids, thereby severely limiting their technical use [Takenaka, S., Dohtsu, K., Takagi, M., Anal. Sci. 8:3–7 (1992)].

The tris-4,4',4"-methoxytrityl group is too labile for the oligonucleotide synthesis and is removed under the coupling conditions of the phosphite triester process [Beaucage, S. L., Iyer, R., Tetrahedron 48:2233 (1992)]. The 4,4',4"-tris (benzoyloxy)trityl (TBTr) group and the 4,4',4"-tris(4,5-dichlorophthalimido)trityl (CPTr) group are too troublesome for general use because of the complicated conditions for their preparation and removal, especially in their automatated synthesis [Beaucage, S. L., Iyer, R., Tetrahedron 48:2235 (1992)]. Other trityl groups [Beaucage, S. L., Iyer, R., Tetrahedron 48:2236 (1992)] permit the derivatisation of the nucleoside monomers in only modest yields. Crystallisation of the derivatives is usually impossible.

Surprisingly, it has now been found that nucleosides and nucleoside analogs are obtained as easily purifiable amorphous or crystalline solids by protecting the 5'-hydroxy group with tris-4,4',4"-tert-butylphenylmethyl (=tris-4,4',4"-tert-butyltrityl or TFTr). It has also surprisingly been found that oligonucleotides which carry a TTTr group at their 5'-terminus are substantially easier to purify, especially by chromatographic methods such as reversed phase HPLC.

In one of its aspects, the invention relates to nucleosides, nucleoside analogs, nucleotides, nucleotide analogs or oligonucleotides from at least two such identical or different nucleotides and/or nucleotide analogs that carry an unsubstituted or substituted residue of a nucleobase B and one primary protected hydroxyl group, the protective group being TTTr.

The TTTr group itself is known. Marvel et al. [Marvel, C. S., Kaplan, J. F., Himel, C. M., J. Am. Chem. Soc. 63:1892–1896 (1941)] disclose TTTrCl, TTTrOH and peroxides of the TTTr group in connection with the dissociation behaviour of alkyl-substituted hexaarylethanes. Ashton et al. [Ashton, P. R., Philp, D., Spencer, N., Stoddart, J. F., J. Chem. Soc., Chem. Commun. 1124–1128 (1992)] describe the TTTr group as blocking group in the construction of mechanisms in the nanometer range, in particular in the construction of so-called rotaxanes and pseudorotaxanes.

As novel protective group in nucleic acid chemistry, the TTTr protective group is distinguished by the surprising ease with which it can be introduced, which introduction is effected with greater regioselectivity than with the customary DMTr and pixyl groups. The nucleosides and nucleoside analogs can often be isolated from the reaction mixtures without chromatography, so that they can be very advantageously used for the large-scale preparation of nucleoside units for DNA synthesis (automated syntheses). Furthermore, the novel oligonucleotides can be more easily purified by known methods, conveniently by reversed phase HPLC, than those oligonucleotides that carry the customary protective groups.

The TTTr group can be used simultaneously with the standard known protective groups of oligonucleotide chemistry [Beaucage, S. L., Iyer, R., Tetrahedron 48:Tables 1 to 3 (1992)], conveniently with a protective group of free amino groups in the nucleobases, for example with an unsubstituted or substituted cycloalkylcarbonyl group containing 3 to 12, preferably 4 to 8, most preferably 5 or 6, ring carbon atoms, preferably with the cyclohexanecarboxyl group (CC), or the amidine protective group, typically the dimethylaminomethylidene group. The nucleosides and nucleoside analogs of this invention are suitable building blocks for oligonucleotide synthesis by solid-phase processes and even by a process in solution.

A whole host of suitable nucleosides, nucleoside analogs, nucleotides, nucleotide analogs or oligonucleotides within the scope of this invention carrying preferably a secondary OH group for effecting linkage of the nucleotide bond are known and described in the technical literature, for example in Townsend, L. B. (Hrsg.), Chemistry of Nucleosides and Nucleotides 1, Plenum Press, New York (1988), or can be prepared by known processes. They may generally consist of an open-chain carbon backbone interrupted by —O— or —S— or of a carbocyclic or O- or S-heterocyclic structure with a nucleobase B. The nucleosides may be natural or synthetic nucleosides.

The open-chain carbon backbone may conveniently contain 3 to 12, preferably 3 to 6, carbon atoms. The carbocyclic and heterocyclic structures may typically be monocyclic ring systems containing 3 to 12, preferably 3 to 8 and, most preferably, 4 or 5 ring carbon atoms. They may also be bicyclic to tetracyclic systems containing 5 to 16, preferably 8 to 16, carbon atoms. The structures may contain further substituents, typically protected OH groups.

In a preferred embodiment of the invention the nucleosides are 5-membered carbocycles or furans.

If the nucleobase B is a purine radical or an analog thereof, said radical may be a radical of formula I, Ia, Ib, Ic, Id or Ie

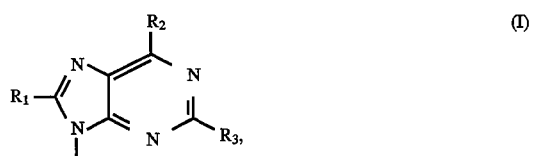

-continued

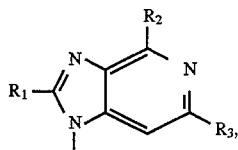
(Ib)

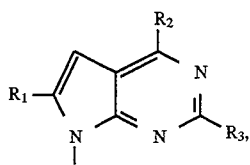
(Ic)

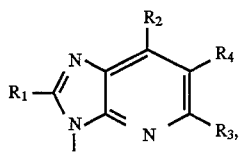
(Id)

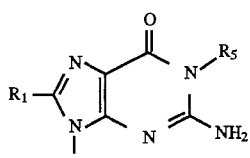
(Ie)

wherein $R_1$ is H, Cl, Br, $NH_2$ or OH, and $R_2$, $R_3$ and $R_4$ are each independently of one another H, OH, SH, $NH_2$, $NHNH_2$, NHOH, NHOalkyl of 1 to 12 carbon atoms, F, Cl, Br, alkyl or hydroxyalkyl or aminoalkyl or alkoxy or alkylthio of 1 to 12 carbon atoms, in which radicals the hydroxyl and amino groups are unsubstituted or substituted by a protective group, or are phenyl, benzyl, primary amino containing 1 to 20 carbon atoms or secondary amino containing 2 to 30 carbon atoms, and $R_5$ is H or $C_1$–$C_4$alkyl.

Primary amino preferably contains 1 to 12, most preferably 1 to 6, carbon atoms, and secondary amino preferably contains 2 to 12, most preferably 2 to 6, carbon atoms.

Illustrative examples of alkyl, alkoxy, alkylthio, hydroxyalkyl and aminoalkyl which preferably contain 1 to 6 carbon atoms are methyl, ethyl and the isomers of propyl, butyl, pentyl, hexyl, heptyl, octyl, nonyl, decyl, undecyl and dodecyl, as well as corresponding alkoxy, alkylthio, hydroxyalkyl and aminoalkyl radicals. Alkyl, alkoxy, alkylthio, hydroxyalkyl and aminoalkyl preferably each contain 1 to 4 carbon atoms. Preferred alkyl, alkoxy, alkylthio, hydroxyalkyl and aminoalkyl radicals are methyl, ethyl, n- und isopropyl, n-, iso- and tert-butyl, methoxy, ethoxy, methylthio and ethylthio, aminomethyl, aminoethyl, hydroxymethyl and hydroxyethyl.

Primary amino and secondary amino may typically be radicals of formula $R_6R_7N$, wherein $R_6$ is H or independently has the meaning of $R_7$, and $R_7$ is alkyl, aminoalkyl, hydroxyalkyl each containing 1 to 20, preferably 1 to 12 and, most preferably, 1 to 6, carbon atoms; carboxyalkyl or carbalkoxyalkyl in which the carbalkoxy moiety contains 2 to 8 carbon atoms and the alkyl moiety contains 1 to 6, preferably 1 to 4, carbon atoms; alkenyl of 2 to 20, preferably 2 to 12 and, most preferably, 2 to 6, carbon atoms; phenyl, mono- or di($C_1$–$C_4$alkyl)phenyl or di($C_1$–$C_4$alkoxy)phenyl, benzyl, mono- or di($C_1$–$C_4$alkyl)benzyl or di($C_1$–$C_4$alkoxy)benzyl; or 1,2-, 1,3- or 1,4-imidazolyl-$C_1$–$C_6$alkyl, or $R_6$ and $R_7$, taken together, are tetra- or pentamethylene, 3-oxa-1,5-pentylene, —$CH_2$—$NR_8$—$CH_2CH_2$— or —$CH_2CH_2$—$NR_8$—$CH_2CH_2$—, wherein $R_8$ is H or $C_1$–$C_4$alkyl. The amino group in aminoalkyl may be substituted by one or two $C_1$–$C_4$alkyl or $C_1$–$C_4$hydroxyalkyl groups. The hydroxyl group in hydroxyalkyl is free or etherified with $C_1$–$C_4$alkyl.

Examples of alkyl groups have been cited above. Illustrative examples of aminoalkyl are aminomethyl, aminoethyl, 1-aminoprop-2- or -3-yl, 1-aminobut-2-, -3- or -4-yl, N-methyl- or N,N-dimethyl- or N-ethyl- or N,N-diethyl- or N-2-hydroxyethyl- or N,N-di-2-hydroxyethylaminomethyl, -aminoethyl, -aminopropyl or -aminobutyl. Hydroxyalkyl is typically hydroxymethyl, 1-hydroxy-eth-2-yl, 1-hydroxyprop-2- or -3-yl, 1-hydroxybut-2-, -3- or -4-yl. Exemplary carboxyalkyl groups are carboxymethyl, carboxyethyl, carboxypropyl and carboxybutyl, and carbalkoxyalkyl is typically carbalkoxyalkyl esterified with methyl or ethyl. Alkenyl is typically allyl, but-1-en-3- or -4-yl, pent-3- or 4-en-1- or -2-yl, hex-3- or -4- or -5-en-1- or -2-yl. Illustrative examples of alkyl- and alkoxyphenyl and alkyl- and alkoxybenzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Imidazolylalkyl in which the alkyl moiety preferably contains 2 to 4 carbon atoms may typically be 1,2-, 1,3- or 1,4-imidazolylethyl or -n-propyl or -n-butyl. $R_8$ is preferably H, methyl or ethyl.

Preferred examples of primary amino and secondary amino are methylamino, ethylamino, dimethylamino, diethylamino, allylamino, mono- or di-(1-hydroxy-eth-2-yl)amino, phenyl- and benzylamino, acetylamino and benzoylamino.

In a preferred embodiment $R_1$ is hydrogen. In another preferred embodiment $R_4$ is hydrogen. In yet a further preferred embodiment $R_2$ and $R_3$ are each independently of the other H, F, Cl, Br, OH, SH, $NH_2$, NHOH, $NHNH_2$, methylamino, dimethylamino, benzoylamino, methoxy, ethoxy and methylthio.

Besides purine, typical examples of analogs of the purine series are adenine, N-methyladenine, N-benzyladenine, 2-methyladenine, 2-methylthioadenine, 2-aminoadenine, 3-carbaadenine, 7-carbaadenine, 1-carbaadenine, 6-hydroxypurine, 2-amino-6-chloropurine, 2-amino-6-methylthiopurine, 2-amino-6-hydroxypurine, 3-carba-6-chloropurine, guanine, 2-methylguanine. Adenine, 2-aminoadenine and guanine are particularly preferred.

If the nucleobase B is the radical of a pyrimidine analog, said radical is a radical of formula II, IIa and IIb

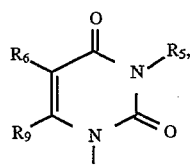
(II)

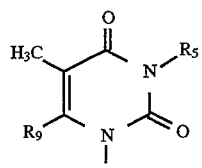
(IIa)

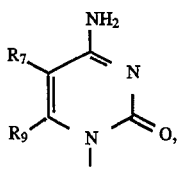

wherein $R_5$ is H or $C_1$–$C_4$alkyl, and $R_6$, $R_7$ and $R_9$ each independently of one another have the meanings previously given for $R_2$, including the preferred meanings, and the hydrogen toms of the $NH_2$ group in formula IIb may be substituted by $C_1$–$C_6$alkyl or benzoyl, as well as the dihydro derivatives of the radicals of formulae II, IIa and IIb. Preferably $R_6$ is H, $C_1$–$C_6$alkyl or hydroxyalkyl, F, Cl, Br, $NH_2$, benzoylamino, mono- or di-$C_1$–$C_6$alkylamino, and $R_7$ is preferably H, $C_1$–$C_6$alkyl or $C_1$–$C_6$alkoxy or $C_1$–$C_6$hydroxyalkyl, F, Cl, Br, $NH_2$, benzoylamino, mono- or di-$C_1$–$C_6$alkylamino.

$R_5$ is preferably H or methyl. $R_6$ is preferably H, F, Cl, Br, $NH_2$, $NHCH_3$, $N(CH_3)_2$ or $C_1$–$C_4$alkyl. $R_7$ is preferably H, $C_1$–$C_4$alkyl, more particularly methyl, or $NH_2$, $NHCH_3$ or $(CH_3)_2N$ dar.

Illustrative examples of pyrimidine analogs are uracil, thymine, cytosine, 5-fluorouracil, 5-chlorouracil, 5-bromouracil, dihydrouracil, pseudouracil, 1-methylpseudouracil, 5-methyluracil, 3-methylcytosine and 5-methylcytosine.

Within the scope of this invention, protective groups for nucleobases will be understood as meaning the protective groups commonly known in the art. Typical examples of such protective groups are: $C_1$–$C_8$alkyl; mono- or bicyclic $C_7$–$C_{12}$aralkyl; mono- or bicyclic $C_7$–$C_{12}$aralkoxy; mono- or bicyclic $C_7$–$C_{12}$haloaralkyl; diphenylmethyl; diphenylmethyl which is substituted by 1 to 4 methyl or methoxy groups; triphenylmethyl; triphenylmethyl which is substituted by 1 to 6 methyl or methoxy groups or by 1 to 3 tert-butyl groups; xanthenyl which is substituted by phenyl or naphthyl; —Si($R_{10}$)($R_{11}$)($R_{12}$), wherein ($R_{10}$), ($R_{11}$) and ($R_{12}$) are each independently of one another $C_1$–$C_{20}$alkyl, benzyl or phenyl; R—C(O)—, wherein R is $C_1$–$C_6$alkyl, benzyl, benzyl which is substituted by methyl, methoxy or halogen; $C_1$–$C_{12}$alkoxy, $C_1$–$C_{12}$alkoxy which is substituted by fluorene, phenoxy, phenoxy which is substituted by methyl, methoxy or halogen, benzyloxy or benzyloxy which is substituted by methyl, methoxy or halogen; $R_{13}$—$SO_{02}$—, wherein $R_{13}$ is $C_1$–$C_{12}$alkyl, $C_5$–$C_6$cycloalkyl, phenyl, phenyl which is substituted by $C_1$–$C_{12}$alkyl or halogen, benzyl or benzyl which is substituted by $C_1$–$C_{12}$alkyl or halogen; $C_1$–$C_{12}$alkoxyacetyl or phenoxyacetyl which is unsubstituted or substituted by one or more than one identical or different member selected from the group consisting of linear or branched $C_1$–$C_6$alkyl, $C_1C_6$haloalkyl, halogen, $C_1$–$C_6$alkoxy, $C_1$–$C_6$alkylthio, nitro and cyano; cycloalkylcarbonyl containing 3 to 12 ring carbon atoms; $C_{-C_6}$alkyl- or $C_1$–$C_6$alkoxy-substituted cycloalkylcarbonyl containing 3 to 12 ring carbon atoms; or amidine protective groups, for example the dimethylaminomethylidene group.

As already mentioned, preferred protective groups are the cycloalkylcarbonyl group containing 3 to 12, preferably 4 to 8, most preferably 5 or 6, ring carbon atoms, in particular the cyclohexanecarboxyl group, and the dimethylaminomethylidene group.

$C_1$–$C_8$Alkyl is typically methyl, ethyl, n- and isopropyl, n-, iso- and tert-butyl; monocyclic $C_7$–$C_{12}$aralkyl is typically benzyl, methylbenzyl, dimethylbenzyl; mono- or bicyclic $C_7$–$C_{12}$aralkoxy may be methoxybenzyl, dimethoxybenzyl; mono- or bicyclic $C_7$–$C_{12}$haloalkyl is bromobenzyl; substituted diphenylmethyl is typically di(methylphenyl)methyl, di(dimethylphenyl)methyl, di(methoxyphenyl)methyl, di(dimethoxyphenyl)methyl; substituted triphenylmethyl is typically tri(methylphenyl)methyl, tri(dimethylphenyl)methyl, tri(methoxyphenyl)methyl, tri(dimethoxyphenyl)methyl, monomethoxytrityl, dimethoxytrityl and tris-p-tert-butylphenylmethyl; silyl groups typically include triphenylsilyl, trimethylsilyl, triethylsilyl, tri-n-propylsilyl, isopropyldimethylsilyl, tert-butyldimethylsilyl, tert-butyldiphenylsilyl, n-octyldimethylsilyl and (1,1,2,2-tetramethylethyl)dimethylsilyl; the group R—C(O)— will typically be acetyl, trifluoroacetyl, propanoyl, butanoyl, pentanoyl, hexanoyl, benzoyl, methylbenzoyl, methoxybenzoyl, chlorobenzoyl, bromobenzoyl, methoxycarbonyl, ethoxycarbonyl, n- or isopropoxycarbonyl or n-, iso- or tert-butoxycarbonyl, or phenoxycarbonyl, benzyloxycarbonyl, methylphenoxycarbonyl or methoxyphenoxycarbonyl or chlorophenoxy- or -benzyloxycarbonyl, 9-fluorenylmethoxycarbonyl, allyloxycarbonyl, cinnamoyloxycarbonyl, 2,2,2-trichloroethoxycarbonyl, trimethylsilylethoxycarbonyl, chloroethoxycarbonyl, bromoethoxycarbonyl, morpholinoethoxycarbonyl; and the group $R_{13}$—$SO_2$— will typically be methylsulfonyl, ethylsulfonyl, propylsulfonyl, butylsulfonyl, phenylsulfonyl, benzylsulfonyl, p-bromosulfonyl, p-methoxysulfonyl and p-methylphenylsulfonyl; and alkoxyacetyl and phenoxyacetyl are typically methoxyacetyl, ethoxyacetyl, phenoxyacetyl, (p-methylphenoxy)acetyl, (p-tert-butylphenoxy)acetyl.

Within the scope of this invention, particularly suitable nucleosides or nucleotides have one of the following formulae IIIa, IIIb, IIIc or IIId

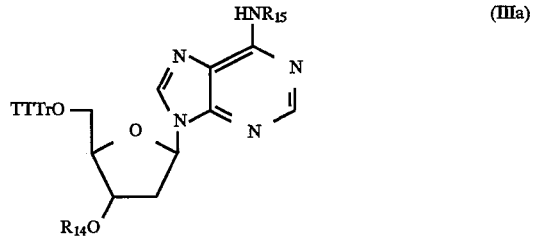

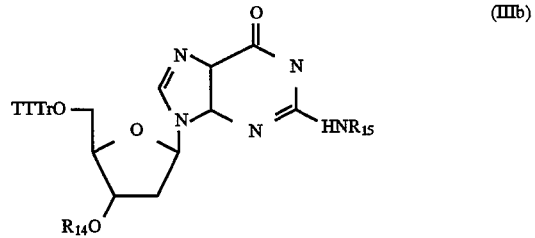

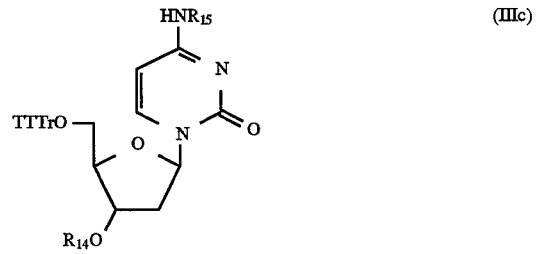

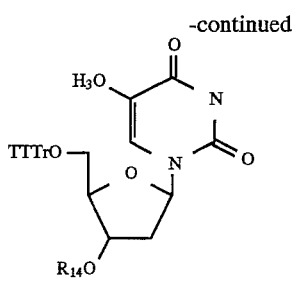

(IIId)

wherein $R_{14}$ is hydrogen or a radical which forms a nucleotide linking group and $R_{15}$ is hydrogen or cyclohexylcarbonyl.

Within the scope of this invention, particularly suitable nucleotides are those in which $R_{14}$ in formulae IIIa, IIIb, IIIc and IIId are a phosphorus-containing radical of formula IVa, IVb or IVc

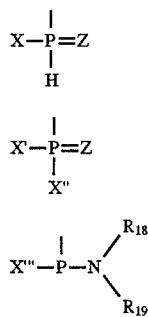

which forms a nucleotide linking group, wherein

Z is oxygen or sulfur;

X, X' and X" are each independently of one another oxygen or sulfur carrying a negative charge, with counterion Li, Na, K, Cs, tertiary or quanenary ammonium; or X' and X" are each independently of the other $C_1-C_{12}$alkyl, $C_6-C_{12}$aryl, $C_7-C_{20}$aralkyl, $C_7-C_{20}$alkaryl, $-OR_b$ or $-SR_b$;

X''' is $C_1-C_{12}$alkyl, $C_6-C_{12}$aryl, $C_7-C_{20}$aralkyl, $C_7-C_{20}$alkaryl, $-OR_b$ or $-SR_b$; and $R_b$ is $C_1-C_{12}$alkyl, $C_6-C_{12}$aryl, $C_7-C_{20}$aralkyl, $C_7-C_{20}$alkaryl;

$R_{18}$ and $R_{19}$ are each independently of the other hydrogen, $C_1-C_{12}$alkyl, $C_2-C_{12}$alkenyl, $C_6-C_{12}$aryl, $C_7-C_{20}$aralkyl or $C_7-C_{20}$alkaryl;

and alkyl, aryl, aralkyl and alkaryl in the definitions of $R_{18}$, $R_{19}$ and $R_b$ are unsubstituted or substituted by alkoxy, alkylthio, halogen, $-CN$, $-NO_2$, phenyl, nitrophenyl or halophenyl.

Tertiary and quartenary ammonium will be understood as meaning an ion of formula $R_fR_gR_hR_iN^{\oplus}$, in which the nitrogen of the cation may be a member of saturated or unsaturated mono- to tricyclic ring systems, and $R_f$ is alkyl or aminoalkyl, each of 1 to 20, preferably 1 to 12 and, most preferably, 1 to 6, carbon atoms; carboxyalkyl or carbalkoxyalkyl, in which the carbalkoxy group contains 2 to 8 carbon atoms and the alkyl group 1 to 6, preferably 1 to 4, carbon atoms; alkenyl of 2 to 20, preferably 2 to 12 and, most preferably, 2 to 6, carbon atoms; phenyl, mono- or di($C_1-C_4$alkyl)phenyl or di($C_1-C_4$alkoxy)phenyl, benzyl, mono- or di($C_1-C_4$alkylbenzyl or di($C_1-C_4$alkoxy)benzyl; or 1,2-, 1,3- or 1,4-imidazolyl-$C_1-C_6$alkyl; and $R_g$, $R_h$ and $R_i$ are each independently of one another hydrogen or have the meaning of $R_f$ or $R_f$ and $R_g$, taken together, are alkylidene, tetra- or pentamethylene, 3-oxa-1,5-pentylene, $-CH_2-NR_e-CH_2CH_2-$ or $-CH_2CH_2-NR_e-CH_2CH_2-$, wherein $R_e$ is H or $C_1-C_4$alkyl, and $R_h$ and $R_i$ each independently of the other have the meaning of $R_f$. The amino group in aminoalkyl can be substituted by one or two $C_1-C_4$alkyl groups.

Illustative examples of carboxyalkyl are carboxymethyl, carboxyethyl, carboxypropyl and carboxybutyl, and carbalkoxyalkyl is typically carbalkoxyalkyl esterified with methyl or ethyl. Alkenyl is typically allyl, but-1-en-3- or -4-yl, pent-3- or 4-en-1- or -2-yl, hex-3- or -4- or -5-en-1- or -2-yl. Illustrative examples of alkyl- and alkoxyphenyl and alkyl- and alkoxybenzyl are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Imidazolylalkyl in which the alkyl moiety preferably contains 2 to 4 carbon atoms may typically be 1,2-, 1,3- or 1,4-imidazolylethyl or -n-propyl or -n-butyl.

Illustrative examples of $R_{18}$, $R_{19}$ and $R_b$ as alkyl are methyl, ethyl and the isomers of propyl, butyl, pentyl, hexyl, heptyl and octyl. $R_{18}$, $R_{19}$ und $R_b$ as aryl are typically phenyl and naphthyl. $R_{18}$ and $R_{19}$ as alkenyl are typically allyl and ($C_1-C_4$alkyl)CH=CH—CH$_2$—. Illustrative examples of $R_{18}$, $R_{19}$ and $R_b$ as aralkyl are phenyl—$C_nH_{2n}$—, in which n is an integer from 1 to 6, preferably benzyl. Illustrative examples of $R_{18}$, $R_{19}$ and $R_b$ as alkaryl are mono-, di- and tri($C_1-C_4$alkyl)phenyl. Preferred substituents are chloro, bromo, methoxy, $-NO_2$, $-CN$, 2,4-dichlorophenyl and 4-nitrophenyl. Typical examples of $R_b$ are 2,2,2-trichloroethyl, 4-chlorophenyl, 2-chlorophenyl and 2,4-dichlorophenyl.

In a particularly preferred embodiment, $R_b$ is β-cyanoethyl, $R_{18}$ and $R_{19}$ are di(isopropyl) and X''' is O.

The nucleotides and oligonucleotides may be covalently bonded through a linking group to a solid carrier material. Suitable carrier materials are typically silica gels, controlled pore glass, polystyrene, polyacrylamide, polyurethanes, polyolefins, polyamides, polyethers and etherified or acylated cellulose derivatives. Depending on the choice of carrier material, the linking group may be derived from dicarboxylic acids, diurethanes or alkoxysilylurethanes. Prepared, loaded carrier materials are commercially available.

The introduction of the TTFr protective groups is carried out in general accordance with a process described by Gait et al. [Gait, M. J., Matthes, H. W. D., Singh, M., Sproat, B. S., Titmas, R. C., in: Gassen, H. G., Lang, A. (Hrsg.) Chemical and Enzymatic Synthesis of Gene Fragments, Verlag Chemie, Weinheim 1–42 (1982)]. Amino protective groups, preferably acyl groups, are conveniently introduced before the TTTr group. To achieve this, the unprotected nucleosides can be exhaustively silylated by treatment with trialkylchlorosilane, for example trimethylchlorosilane, tert-butyldimethylchlorosilane or triisopropylchlorosilane, or tetraalkyldisiloxane, typically 1,1,3,3-tetraisopropyl-1,3-dichlorodisiloxane, in a suitable aprotic, polar, basic solvent such as pyridine, N-methylmorpholine, dimethyl formamide, acetonitrile or tetrahydrofuran, at room temparature. Silylation is then followed by the reaction preferably with an unsubstituted or substituted cycloalkylcarbonyl chloride or with dimethylaminomethylidene, such that only the amino functions of the nucleobase are acylated. Solvolysis of the silyl groups by treatment with suitable nucleophilic agents, typically with aqueous ammonium, $OH^{\ominus}$ or $F^{\ominus}$, preferably aqueous ammonium fluoride, is subsequently carried out. After removal of the solvent, the acylated nucleosides can be easily isolated on the basis of their solubility characteristics.

The introduction of the TTTr group is effected by reacting the preferably acylated nucleoside with tris-4,4',4"-tert-butyltrityl chloride, conveniently in the presence of a sterically hindered tertiary amine in a suitable aprotic, polar, basic solvent such as pyridine, N-methylmorpholine, dimethyl formamide, acetonitrile or tetrahydrofuran, preferably pyridine. The solubility characteristics of the educts enable the products to be easily separated. Excess tritylating reagent can be removed by digestion with petroleum ether, preferably with the fraction having the boiling range from 40° to 60° C.

The novel nucleosides can be further convened by known methods into phosphoroamidite, H-phosphonate or triester derivatives that are suitable for oligonucleotide syntheses by solid phase processes and by processes in solution.

In another of its aspects, the invention relates to a process for the preparation of oligonucleotides of formula V

5'—OH(U)$_m$(V)$_n$OH—3'  (V)

wherein U and V are identical or different, natural or synthetic nucleoside residues and m and n are each independently of the other 0 or an integer from 1 to 200, and the sum of m and n is 2 to 200, by (a) reacting a compound of formula VI

R$_{20}$—O—(U')$_{m'}$(V')$_{n'}$OR$_{21}$—3'  (VI)

wherein R$_{20}$ is a protective group and U' and V' have the meanings of U and V, m' and n' are each independently of the other 0 or an integer from 1 to 199, and the sum of m' and n' is 2 to 199, and R$_{21}$ is a phosphorus-containing radical of formula IVa, IVb or IVc

$$\begin{array}{c} | \\ X-P=Z \\ | \\ H \end{array}$$ (IVa)

$$\begin{array}{c} | \\ X'-P=Z \\ | \\ X'' \end{array}$$ (IVb)

$$\begin{array}{c} | \quad R_{18} \\ | \quad / \\ X'''-P-N \\ \quad \backslash \\ \quad R_{19} \end{array}$$ (IVc)

which forms a nucleotide linking group, wherein

Z is oxygen or sulfur;

X, X' and X" are each independently of one another oxygen or sulfur carrying a negative charge, with counterion Li, Na, K, Cs, tertiary or quartenary ammonium; or X' and X" are each independently of the other $C_1$–$C_{12}$alkyl, $C_6$–$C_{12}$aryl, $C_7$–$C_{20}$aralkyl, $C_7$–$C_{20}$alkaryl, —OR$_b$ or —SR$_b$;

X'" is $C_1$–$C_{12}$alkyl, $C_6$–$C_{12}$aryl, $C_7$–$C_{20}$aralkyl, $C_7$–$C_{20}$alkaryl, —OR$_b$ or —SR$_b$; and R$_b$ is $C_1$–$C_{12}$alkyl, $C_6$–$C_{12}$aryl, $C_7$–$C_{20}$aralkyl, $C_7$–$C_{20}$alkaryl;

R$_8$ and R$_{19}$ are each independently of the other hydrogen, $C_1$–$C_{12}$alkyl, $C_2$–$C_{12}$alkenyl, $C_6$–$C_{12}$aryl, $C_7$–$C_{20}$aralkyl or $C_7$–$C_{20}$alkaryl;

and alkyl, aryl, aralkyl and alkaryl in the definitions of R$_{18}$, R$_{19}$ and R$_b$ are unsubstituted or substituted by alkoxy, alkylthio, halogen, —CN, —NO$_2$, phenyl, nitrophenyl or halophenyl, with a compound of formula VII

5'—OH(U")$_{m''}$(V")$_{n''}$-O—R$_{22}$  (VII)

wherein U" and V" have the meanings of U and V, m" and n" are each independently of the other 0 or an integer from 1 to 198, and the sum of m" and n" is 2 to 198, and R$_{22}$ is (i) a radical of formula IVb, wherein Z is oxygen or sulfur; X' and X" are each independently of the other $C_1$–$C_{12}$alkyl, $C_6$–$C_{12}$aryl, $C_7$–$C_{20}$aralkyl, $C_7$–$C_{20}$alkaryl, —OR$_b$ or —SR$_b$; and R$_b$ is $C_1$–$C_{12}$alkyl, $C_6$–$C_{12}$aryl, $C_7$–$C_{20}$aralkyl, $C_7$–$C_{20}$alkaryl, and alkyl, aryl, aralkyl and alkaryl as defined for R$_b$ are unsubstituted or substituted by alkoxy, alkylthio, halogen, —CN, —NO$_2$, phenyl, nitrophenyl or halophenyl;

(ii) a hydroxyl protective group; or (iii) a linkage to a solid carrier material by means of a linking group;

(b) if necessary, repeating step (a) until an oligonucleotide of the desired length has formed, and, before each coupling, removing the protective group R$_{20}$, capping any free hydroxyl groups present, and then oxidising the resultant phosphite to the phosphate, (c) if desired, detaching or isolating the oligonucleotide, and (d) removing the residual protective group R$_{20}$, said protective group R$_{20}$ being TTTr.

A very particularly preferred embodiment of the process comprises preparing oligonucleotides of formula V, wherein the sum of m and n is 2 to 50, preferably 2 to 30. The nucleosides in the oligonucleotide are usually linked through ester groups. Illustrative examples are phosphorothioates, phosphorodithioates, phosphoroamidates, alkylphosphonates, hydrogenphosphonates, phosphates, carbonates and carbamates.

The process can be carried out as solid phase process or as process in solution. Both processes are known per se and are usually carried out in the temperature range from −20° C. to 100° C., preferably from 10° C. to 60° C. It is expedient to carry out the reaction in the presence of an inert solvent. Illustrative examples of inert solvents are acetoniuile, pyridine, dioxane, dimethyl formamide, ethylene glycol dimethyl ether, diethylene glycol dimethyl ether, chloroform, trichloroethan, dichloromethane, N-methylpyrrolidone, tetrahydrofuran, dibutyl ether and diethyl ether. If the process is carried out as solid phase process, the synthesis is conveniently conducted with a commercially available DNA synthesizer with the reagents described by and likewise obtainable from the respective manufacturer, i.e. solvent, capping solution, oxidation solution, coupling reagent and detritylation solution, as well as a prepared compound of formula VII.

Hydroxyl protective groups in connection with R$_{21}$ will be understood as meaning the protective groups named in connection with the nucleobases, excluding the amidines.

Solid carrier materials have been described hereinabove. The final oligonucleotides can be removed from the carrier material with aqueous saturated ammonia solution, while deprotecting the oligonucleotides at their nucleobases. This process is also suitable for the simultaneous removal of the cycloalkylcarboxylic acid protective group.

The TTTr protective group is expediently removed under acidic conditions, conveniently with dichloroacetic acid, trichloroacetic acid, trifluoroacetic acid, acetic acid, $ZnBr_2$, boron trifluoride dietherate.

Capping any free hydroxyl groups present is effected by known processes, conveniently using acetic anhydride oxidation of the phr 2,6-lutidine.

The oxidation of the phosphite to the phosphate is conveniently carried out with an aqueous iodine solution or tert-butyl hydroperoxide in acetonitrile.

The final oligonucleotide can be isolated by chromatography or electrophoresis. Isolation by reversed phase HPLC is advantageous.

In another of its aspects, the invention relates to the use of the novel nucleosides, nucleoside analogs, nucleotides, nucleotide analogs and oligonucleotides in a process for the preparation of of oligonucleotides of formula V.

The use of the TTTr group has special advantages for purifying oligonucleotides. It has furthermore been found that the novel protected oligonucleotides are distinguished by their greater stability in aqueous neutral buffer systems over the oligonucleotides which are protected by the customary 4,4'-dimethoxytrityl groups, so that the detritylation losses during purification, especially purification by HPLC, are lower.

The following Examples illustrate the invention in more detail.

A: Preparation of the starting compounds

EXAMPLE A1

Preparation of $N^2$-cyclohexylcarbonyl-2'-deoxyguanosine 28 g of deoxyguanosine are taken up in 3×200 ml of absolute pyridine and the solution is then concentrated to dryness under vacuum at 50° C. The nucleoside is taken up with 340 ml of diisopropylethylamine and to the solution are added 127 ml of trimethylchlorosilane. The mixture is stirred for 2 hours at room temperature and then a solution of 100 ml of absolute tetrahydrofuran (THF) and 20.4 ml of cyclohexanecarbonyl chloride is added over 1 hour. The reaction mixture is cooled to 0° C. after 16 hours and 100 ml of methanol are added over 1 hour, followed by the addition of 180 ml of an aqueous 35% solution of ammonium fluoride. One hour after addition of the fluoride, the volatile constituents are removed by evaporation under vacuum at 50° C. Residual pyridine is removed by coevaporation with 2×200 ml of toluene. The crude product is stirred with 700 ml of ice-water for 30 minutes and then filtered. The filter cake is treated in 700 ml of a boiling solution of ethanol/water (7:3 v/v). Insoluble matter is filtered off hot. The title compound precipitates from the cooled filtrate and is vacuum dried.

$^1$H-NMR:(DMSO) 8.14: s, $H^8$; 6.21: t, 1'; 5.34, 4.97: 2H s (broad) OH; 4.88: m, 3'; 3.8: m, 4'; 2.5: 2H: 2'-, H1 of CC group; 2.26: m, 2'; 1.1–1.9: 10H, m, CC group.

EXAMPLE A2

Preparation of $N^4$-cyclohexylcarbonyl-2'-deoxycytidine 5.3 g of deoxycytidine are taken up in 3'100 ml of absolute pyridine and the solution is then concentrated to dryness at 55° C. under a high vacuum. The dried educt is taken up in 100 ml of absolute pyridine and to the solution are added 25.4 ml of trimethylchlorosilane. The mixture is stirred for 2 hours and then a solution of 6.3 g of cyclohexanecarbonyl chloride in 40 ml of absolute THF is added dropwise. The reaction mixture is stirred for 18 hours at room temperature and then, while cooling with ice, 20 ml of methanol are slowly added. Desilylation is effected by adding 36 ml of water from a 35% aqueous solution of ammonium fluoride. After 60 minutes, the reaction mixture is concentrated to dryness at 55° C. under vacuum. Residual pyridine is removed by co-evaporation with 2×100 ml of water. The crude product is taken up in 100 ml of water and extracted with 3×100 ml of n-butanol. The butanol phases are combined, dried over sodium sulfate, and concentrated to an oil at 55° C. under vacuum. The oil is stirred for 5 hours in 500 ml of ether, whereupon crystals of the title compound precipitate. The crystals are collected by suction filtration and dried under a high vacuum.

$^1$H-NMR (CD$_3$OD): 8.47 d, $H^6$; 7.44: d, $H^5$; 6.22: q, 1'; 4.4, 4.03: 3', 4'; 3,7–3.9: 2H, m, 5'; 2.35–2.55: 2H: m, 2', C-1, CC group; 2.07–2.25: m, 2'; 1.4–1.9, 1.1–1.65: 10H, m, CC group.

EXAMPLE A3

Preparation of $N^6$-cyclohexylcarbonyl-2'-deoxyadenosine 5.4 g of deoxycytidine are taken up in 3×100 ml of absolute pyridine and the solution is then concentrated to dryness at 55° C. under a high vacuum. The dried educt is taken up in 100 ml of absolute pyridine and to the solution are added 68 ml of diisopropylethylamine. Then 25.4 ml of trimethylchlorosilane are added. The mixture is stirred for 2 hours and then a solution of 6.3 g of cyclohexanecarbonyl chloride in 40 ml of absolute THF is added dropwise. The reaction mixture is stirred for 18 hours at room temperature and then, while cooling with ice, 20 ml of methanol are slowly added. Desilylation is effected by adding 36 ml of water from a 35% aqueous solution of ammonium fluoride. After 60 minutes, the reaction mixture is concentrated to dryness at 55° C. under vacuum. The crude product is taken up in 100 ml of ethyl acetate and the solution is extracted in sucession with 100 ml of aqueous sodium hydrogencarbonate and wit 100 ml of brine. The organic phase is dried over sodium sulfate and concentrated to an oil under vacuum at 55° C. The title compound is obtained by precipitation from diethyl ether.

$^1$H-NMR (CDCl$_3$): 8.35, 8.33, 2s, adenine; 6.25: t, 1'; 4.34: m, 3'; 3.78: m, 4'; 3.5: 2H, m 5'; 2.55, 2.4, 2.2: 3H, 3m, 2', C-1 CC group; 1.85–1.1: 10H: m, CC group.

Stability of the $N^6$-cyclohexylcarbonyl-2'-deoxyadenosine to the iodine oxidation for the DNA synthesis by the phosphite triester process: 1 g of $N^6$-cyclohexancarbonyl-2'-deoxyadenosine are subjected for 22 hours to a solution comprising 3% iodine, 2% water, 20% pyridine and 75% THF. After this time, a thin-layer chromatogram of the reaction mixture shows no reaction.

B: Preparation of the inventive compounds

EXAMPLE B1

Preparation of 5'-(tris-4,4',4"-tert-butyltrityl)-$N^2$-cyclohexylcarbonyl-2'-deoxyguanosine 27 g of $N^2$-cyclohexylcarbonyl-2'-deoxyguanosine are taken up in 3×200 ml of absolute pyridine and the solution is then concentrated to dryness at 50° C. under a high vacuum. The nucleoside is taken up in 600 ml of absolute pyridine and to the solution are added 100 ml of triethylamine and then 34.4 g of Iris-4,4',4"-tert-butyltrityl chloride. The mixture is stirred for 18 hours and the precipitate is removed by filtration. The filtrate is concentrated to dryness at 50° C. under vacuum. The residue is taken up in 600 ml of dichloromethane and extracted with 2×500 ml of cold saturated sodium hydrogencarbonate solution and then with 500 ml of brine. The organic phase is dried over sodium sulfate, filtered to remove the salt, and the filtrate is concentrated to dryness at 100–200 torr. The product is suspended in 100 ml of hot methanol. The suspension is filtered and the filtrate is cooled to 0° C., whereupon fresh product precipitates. The product is vigorously stirred in 500 ml of petroleum ether for 2 hours and the title compound is isolated by filtration and dried in a vacuum drier at 60° C./30–50 torr.

$^1$H-NMR:(CD$_3$OD) 7.95: H$^8$, 7.15: 12H, TTTr; 6.22: t,1'; 4.47: m, 3'; 3.95: m, 4'; 2.65: m, 2'; 2.2–2.45: m, 2', H1(CC group); 1.8–1.1: 10H, m, CC group; 1.13: 27H, 2s, TTTr group.

EXAMPLE B2

Preparation of 5'-(tris-4,4',4"-tert-butyltrityl)-N$^2$-cyclohexylcarbonyl-2'-deoxyguanosine-3'-(cyanoethyl)phosphorodiisopropylamidite To 27.7 g of 5'-(tris-4,4',4"-tert-butyltrityl)-N2-cyclohexylcarbonyl-2'-deoxyguanosine in 800 ml of abolute acetonitrile are added, under dry argon, 20.6 ml of bis(diisopropylaminocyanoethyl)phosphane and 2.67 g of tetrazole, and the mixture is stirred for 18 hours. Then 8 ml of triethylamine are added and the solvent is removed at 50° C. under vacuum. The crude product is taken up in 500 ml of ethyl acetate and extracted with 2×500 ml of cold saturated sodium hydrogencarbonate and then once with 500 ml of brine. The organic phase is concentrated to dryness under vacuum at 50° C., affording an oil which can be further used direct for the preparation of N-methylmorpholinium-5'-(tris-4,4',4"-tert-butyltrityl)-N$^2$-cyclohexylcarbonyl-2'-deoxyguanosine-3'-(cyanoethyl)phosphorothioate (Example B3). For purification, the product is subjected to flash chromatography on silica gel. The product is eluted with n-hexane: ethyl acetate:N-methylmorpholine (30:69:1 v/v/v). The title compound obtained from the combined fractions is concentrated to dryness at 50° C. under vacuum. Further evaporation of solvent residues under a high vacuum gives a white foam.

$^{31}$P-NMR (CDCl$_3$): 148.3, 147.6; $^1$H-NMR (CDCl$_3$): 7.76, 7.72: 2s H$^8$(guanine); 7.38, 7.2 12H, 2m, TTTr group; 6.12, 1'; 4.65: m, 3'; 2.55, 2.6: 2t: CNE 1.22: 27H, s, TTTr group; 1.1, 0.98: 12H, isopropyl (amidite).

EXAMPLE B3

Preparation of N-methylmorpholinium-5'-(tris-4,4',4"-tert-butyltrityl-N$^2$-cyclohexylcarbonyl-2'-deoxyguanosine-3'-(O)-cyanoethylphosphorothioate To 92.2 g of 5'-(tris-tert-butyltrityl)-N$^2$-cyclohexylcarbonyl-2'-deoxyguanosine in 1200 ml of absolute acetonitrile are added, under dry argon, 84 ml of bis(diisopropylaminocyanoethyl)phosphane and 422 ml of a 0.5M tetrazole solution, and the mixture is stirred for 18 hours. Then 16 ml of triethylamine are added and the solvent is stripped off under vacuum at 50° C. The crude product is taken up in 1200 ml of ethyl acetate and extracted with 2×1200 ml of cold saturated sodium hydrogencarbonate and then once with 1200 ml of brine. The organic phase is concentrated to dryness at 50° C. under vacuum, affording an oil. Some impurities of the product can be removed by concentration with 10×200 ml of toluene, so that the crude phosphoroamidite is obtained as a white foam. The crude phosphoroamidite is further reacted using two batches and for further processing mixed with 200 g of crude amidite. The crude amidite is taken up in 1.2 l of acetonitrile and 3.7 ml of water and 77 g of tetrazole are added. The reaction mixture is stirred for 30 minutes and then 77 g of sulfur and 1.2 l of pyridine are added. The reaction solution is stirred for 17 hours at room temperature and concentrated to dryness under vacuum at 50° C. The crude product is extracted with 600 ml of a 1M aqueous solution of N-methylmorpholinium hydrogencarbonate and 600 ml of ethyl acetate, and the precipitated sulfur is filtered off. The organic phase is extracted once more with 2×600 ml of a 1M aqueous solution of N-methylmorpholinium hydrogencarbonate. The organic phase is dried over sodium sulfate and concentrated to dryness at 50° C. under vacuum. The crude product is then subjected to flash chromatography, using a column of 4 kg of silica gel (230–400 mesh). The product is eluted with ethyl acetate:methanol:N-methyl-moropholine (90:9:1, v/v/v). The combined product fractions are concentrated to dryness under vacuum at 50° C. The resultant oil is stirred in 500 ml of n-pentane for 5 hours to give the title compound in powder form. $^{31}$P-NMR(DCCl$_3$):57.21, 56.80 ppm.

EXAMPLE B4

Preparation of 5'-(tris-4,4',4"-tert-butyltrityl) thymidine 3.6 g of thymidine are taken up in 3×25 ml of absolute pyridine and concentrated under vacuum at 55° C. To the dried product so obtained are added 14.8 g of tris-4,4',4"-tert-butyltrityl chloride in 25 ml of dichloromethane at 0° C. over 1 hour. The reaction mixture is stirred for 18 hours at room temperature and then concentrated under a high vacuum. The resultant white foam is taken up in 100 ml of dichloromethane and extracted with 2×100 ml of a cold saturated aqueous solution of sodium hydrogencarbonate and then with 100 ml of brine. The organic phase is dried over sodium sulfate, then concentrated to a white foam. This foam is recrystallised from a mixture of methanol and water (70:30 v/v). The resultant white crystals are filtered with suction and dried under a high vacuum.

$^1$H-NMR: 8.12:N$^3$-H; 7.65: H-6; 7.25: 12H, m, TTTr group; 6.45: t,1'; 4.66: m, 3'; 4.03: 4'; 3.52–3.38: 2H, m, 5'; 2.4: m, 2'; 1.56: 3H, CH$_3^5$; 1.3: 27H, s, TTTr group.

EXAMPLE B5

Preparation of 5'-(tris-4,4',4"-tert-butyltrityl) thymidine-3'-(cyanoethyl) phosphorodiisopropylamidite 7 g of 5'-(tris-4,4',4"-tert-butyltrityl)thymidine are taken up in 3×25 ml of absolute pyridine and the solution is concentrated at 50° C. under a high vacuum. The dried educt so obtained is taken up in 1 l of absolute acetonitrile. To this solution are added 50 ml of bis(diisopropylamino) cyanoethylphosphane and 7.9 g (113 mmol) of tetrazole. The reaction mixture is stirred for 17 hours. Then 38 ml of triethylamine are added. The reaction mixture is concentrated under vacuum at 50° C. The resultant oil is taken up in 500 ml of ethyl acetate and extracted with 2×500 ml of a cold saturated aqueous solution of sodium hydrogencarbonate and then with 500 ml of brine. The organic phase is dried over sodium sulfate and then concentrated to an oil. This oil is dissolved in 1 l of a solution consisting of 99% of methanol and 1% of N-methylmorpholine. With constant stirring and ice cooling, water is slowly added dropwise until the product is precipitated in the form of white crystals. The title compound is isolated by filtration and dried under a high vacuum over $P_4O_{10}$/KOH.

$^1$H-NMR (CDCl$_3$): 7.75:2 s, H$^6$; 7.33: 12H, s, TTTr group; 6.48: m, 1'; 4.78: m, 3'; 4.16, 4.23: 2m, 4'; 3.95–3.3: 2H, m: CNE group, 2H, m: i-Pr (amidite), 2H, m: 5'; 2.9–2.4: 4H: 2H, m: 2', 2H, 2t, CNE group; 1.45–1.15: 42H: t-Bu, TTTr group, CH$_3$, amidite, CH$_3^5$; $^{31}$P-NMR: 148.4, 148.2.

EXAMPLE B6

Preparation of 5'-(tris-4,4',4"-tert-butyltrityl)-N$^2$-cyclohexylcarbonyl-2'-deoxyguanosin-3'-(O)-cyanoethyl-(S) 2,4-dichlorobenzylphosphorthioate 1.4 g of N-methylmorpholinium-5'-(tris-4,4',4"-tert-butyltrityl)-N$^2$-cyclohexanecarbonyl-2'-deoxyguanosin-3'-(O)-cyanoethylphosphorothioate are stirred for 4 days, excluding light, with 0.8 ml of 2,6-lutidine and 1.95 ml of 2,4-dichlorobenzyl chloride in 50 ml of chloroform at room temperature. The product mixture is concentrated to an oil at 50° C. under vacuum. This oil is taken up in 100 ml of dichloromethane and washed in succession twice with an aqueous saturated solution of sodium hydrogencarbonate and once with 100 ml of brine. The organic phase is dried over sodium sulfate and concentrated under vacuum to an oil, which is stirred in petroleum ether/pyridine for 5 hours. The solid title compound so obtained is filtered with suction and dried over $P_4O_{10}$/KOH.

$^{31}$P-NMR (CDCl$_3$): 27.0, 27.6 ppm; PD-MS: [M-DCBn$^+$]$^-$=936; [M+Na$^+$]$^+$=1120; [TTTr]$^+$=412; [G$^{cc}$]$^+$=263

EXAMPLE B7

Preparation of 5'-(tris-4,4',4"-tert-butyltrityl) thymidine-3'-(O)-cyanoethyl-(S)-2,4-dichlorobenzylphosphorothioate 2.7 g of N-methylmorpholinium 5'-(tris-4,4',4"-tert-butyltrityl)thymidine-3'-(O)-cyanoethylphosphorothioate are stirred for 4 days, excluding light, with 1.8 ml of 2,6-lutidine and 4.4 ml of 2,4-dichlorobenzyl chloride in 35 ml of chloroform at room temperature. The mixture is concentrated to an oil at 50° C. under vacuum. This oil is taken up in 100 ml of dichloromethane and washed in succession twice with an aqueous saturated solution of sodium hydrogencarbonate and once with 100 ml of brine. The organic phase is dried over sodium sulfate and concentrated under vacuum to an oil, which is stirred in petroleum ether/pyridine for 5 hours. The solid title compound so obtained is filtered with suction and dried over $P_4O_{10}$/KOH.

$^1$P-NMR (DCCl$_3$): 27.42; 27.24; $^1$H-NMR (CDCl$_3$): 8.6: NH; 7.52: H$^6$; 7.16: 15H, m, TTTr;, 6.45: m, 1'; 5.23: m, 3'; 3.95–4.15: 4H, m, CNE group, DCBn group; 3.32: 2H: m, 5'; 2.3–2.65: 4H, m, CNE group; 2'; 1.2: 30H, 2s, TTTr group, CH$_3^5$.

8 g of 5'-(tris-4,4',4"-tert-butyltrityl)thymidine-3'-(O)-cyanoethyl-(S)-2,4-dichlorobenzylphorothioate are taken up in 25 ml of 3% dichloroacetic acid in dichloromethane and added to a flash chromatography column packed with silica gel. The tris-4,4',4"-tert-butyltritylmethyl ether and the tris-4,4',4"-tert-butyltrityl alcohol are eluted with dichloromethane:methanol:DCA (98:1:1 (v/v/v). Afterwards the product is eluted with dichloromethane:methanol (9:1 (v/v) The fractions are concentrated to an oil at 55° C. under vacuum. The oil is subsequently taken up in 250 ml of ethyl acetate, washed free of dichloroacetate with 5×250 ml of 1M aqueous sodium acetate and dried over sodium sulfate. The solvent is then removed under vacuum, affording thymidine-3'-(O)-cyanoethyl-(S)-2,4-dichlorobenzylphosphorothioate.

$^{31}$P-NMR (CDCl$_3$) 28.15, 27.79; $^1$H-NMR (CDCl$_3$): 8.48: NH; 7.45; 7, 17: 4H, DCBn group, H$^{6,}$ 6.05: m, 1'; 5.13: 3', m; 4.0–4.3: 5H, DCBn group, 4', CNE group; 3.78: m, 5'; 2.7: m,m, CNE group; 2.35: 2'; 1.87: s, CH$_3^5$.

EXAMPLE B8

Preparation of triethylammonium 5'-(tris-4,4',4"-tert-butyltrityl)-thymidine-3'-(S)-dichlorobenzylphosphorothioate 16 g of 5'-(Iris-4,4',4"-tert-butyltrityl)thymidine-3'-(O)-cyanoethyl-(S)-2,4-dichlorobenzylphosporothioate are taken up in 500 ml of a solution of acetonitrile/triethylamine (9:1 v/v). After 2 hours the solution is concentrated under vacuum and the residue is stirred for 2 hours in 500 ml of ether. The product is filtered with suction and dried under a high vacuum, affording the title compound.

$^{31}$P-NMR (CDCl$_3$): 16,69; $^1$H-NMR (CDCl$_3$): 7.58: s, H$^6$; 7.15: 15H, m, TTTr; 6.34: m, 1'; 5.05: m, 3'; 3.85–4.1: 3H, m, 4', DCBn; 3.15: 5'; 2.92: 6H, q, triethylamine; 2.22, 2.3: 2'; 0.9–1.35: m, 39H, TTTr, uiethylamine, CH$_3^5$.

EXAMPLE B9

Preparation of 5'-(tris-4,4',4"-tert-butyltrityl)-N$^6$-pyrrolidinylmethylidene-2'-deoxyadenosine 233 mg of N$^6$-pyrrolidinylmethylidenedeoxyadenosine are taken up in 3×10 ml of absolute pyridine and the solution is then concentrated to dryness under vacuum, such that the temperature does not exceed 50° C. The substance is afterwards taken up in 10 ml of absolute pyridine. With stirring, a solution of 343.8 mg of TTTrCl and 10 ml of dichloromethane is added to this solution at 0° C. over 1 hour. After 60 hours the reaction mixture is concentrated to 2 ml and this residue is run into 100 ml of water. The precipitate is taken up in 100 ml of dichloromethane. The organic phase is extracted with 2×100 ml of an aqueous saturated solution of sodium hydrogencarbonate and then with 100 ml of brine. The washed organic phase is dried over sodium sulfate. The salt is removed and the product is concentrated to dryness. The resultant solid is triturated in 100 ml of petroleum ether (high-boiling) for 1 hour. The product is isolated by filtration, the mother liquor is cooled to 0° C. and further product is isolated by filtration. The filter cake is afterwards washed with cold petroleum ether of 0° C. (high-boiling) and dried under a high vacuum to give the title compound.

$^1$H-NMR (CDCl$_3$): 9.28: s, amidine; 8.62: s, 8.15: s, adenine; 7.4: 12H, m, TTTr;, 6.62:m, 1'; 4.77: m, 3'; 4.22: m 4'; 3.3, 3.82: 2m, 4H pyrrolidinyl; 3.54: d, 2H, 5=; 2.88, 2.55: 2m, 2'; 2H, 2.06: m, 4H, pyrrolidinyl; 1.4: s, 27H, TTTr.

EXAMPLE B10

Preparation of 5'-(tris-4,4',4"-tert-butyltrityl)-N$^2$-dimethylamlnomethylidene-2'-deoxyguanosine 967 mg of N$^2$-dimethylaminomethylidenedeoxyguanosine are taken up in 3×10 ml of absolute pyridine and the solution is then concentrated to dryness under vacuum, such that the temperature does not exceed 50° C. The substance is afterwards taken up in 10 ml of absolute pyridine. With stirring, a solution of 2950 mg of TTTrCl and 10 ml of dichloromethane is added to this solution at 0° C. over 1 hour. After 60 hours the reaction mixture is concentrated to 2 to 3 ml and this residue is run into 100 ml of water. The precipitate is taken up in 100 ml of dichloromethane. The organic phase is extracted with 2×100 ml of an aqueous saturated solution of sodium hydrogencarbonate and then with 100 ml of brine. The washed organic phase is dried over sodium sulfate. The salt is removed and the product is concentrated to dryness. The resultant solid is triturated in 100 ml of petroleum ether (high-boiling) for 1 hour. The product is isolated by filtration, the mother liquor is cooled to 0° C. and further product is isolated by filtration. The filter cake is afterwards washed with cold petroleum ether of 0° C. (high-boiling) and dried under a high vacuum to give the title compound.

$^1$H-NMR (DMSOD$_6$): 11.2, 8.46, 7.75: 2s, amicline, guanine; 7.08: 12H, m, TTTr; 6.12:m, 1'; 5.22: s, OH; 4.37: m, 3'; 3.75: m 4'; 2.96: m, 5H, 5', amidine; 2.89; s, 3H, amidine; 2.5, 2.15: 2m, 2'; 1.08: s, 27H, TTTr.

EXAMPLE B11

Preparation of N-(1-methyl-2-pyrrolidinylmethylidene)-5'-(tris-4,4',4"-tert-butyltrityl)adenosine 50 g of dry adenosine, 20 g of molecular sieve (3 Å), 800 ml of anhydrous methanol and 80 ml of anhydrous pyridine are stirred at room temperature and 29.04 g of distilled N-methylpyrrolidone dimethyl acetal are added. The molecular sieve is removed by filtration. The filtrate is concentrated under vacuum. The residue is concentrated with 3×100 ml of acetoniuile concentrated and dried. This material is dissolved in 450 ml of anhydrous pyridine and 50 g of molecular sieve (5 Å) are added to the solution. The reaction mixture is stirred at 60° C. and 100.3 g of solid tds-4,4',4"-tert-butyltrityl)chloromethane are added. After stirring for 15 hours, the reaction temperature is raised for 5 hours to 70° C. The molecular sieve is removed by filtration and the filtrate is concentrated to dryness. The residue is added to a column of silica gel (ethyl acetate/methanol/N-methylmorpholine 20:2:0.1; diameter 8 cm). The fractions containing the title compound are collected, concentrated and dried.

$^1$H-NMR (250 MHz, CDCl$_3$): 1.27 (s, c. 27 H, 3 (CH$_3$) $_3$C-ar); 2.04 (m, 3H); 2.37 (m,2H); 2.90–3.15 (m, 2H); 3.18 (s, NCH$_3$); 3.2–3.3 (m, 2H); 3.39 (t, c. 1H); 3.51 (t-like m, J=8, 3 H); 3.69 (s, 2H); 4.37 (d-like m, J=5, 1 H); 4.45 (br s, 1H); 4.82 (t, J=5, 1H); 5.99 (d, J=7, H—C(1')); 6.72 (br s, 1H); 7.20 (s, 12H); 8.23 (s) and 8.54 (s)(H—C(2.8).

EXAMPLE B12

Preparation of 5'-(tris-4,4',4"-tert-butyltrityl)-6-methyluracil 40 mmol of 6-methyluracil are dissolved in 75 ml of anhydrous pyridine. The solution is heated to 60° C. and 44 mmol of solid tris-4,4',4"-tert-butyltrityl)chloromethane are added. After stirring for 6 hours at 60° C., the solvent is removed under vacuum and the residue is concentrated once from toluene and twice from acetonitrile. The crude product is dissolved in 600 ml of methyl chloride and washed with 200 ml of saturated NaHCO$_2$ solution. The organic phase is dried over Na$_2$SO$_4$ and the solvents are removed under vacuum. The residue is dissolved in 220 ml of a hot ethanol/water mixture (3:2) and crystallised at 0° C. Melting point: 169°–170° C.

$^1$H-NMR (250 MHz, CDCl$_3$): 1.29 (s, c. 27H, 3 (CH$_3$) $_3$C-ar); 1.38 (s, 3H, CH$_3$C(5);3.14 (br. d, 1H); 3.47 (ABM system, 2H, H$_2$C(5')); 4.22 (d-like m, 1H) and 4.47 (m, 2H)(HC(2', 3',4'); 5.13 (br. s, 1H); 5.96 (d, J=4, 1H, HC(1')); 7.15–7.35 (m, c. 12H,H-(ar)); 7.81 (s, HC(6)); 9.75 (br. s, HN(3)).

EXAMPLE B13

Preparation of 5'-(tris-4,4',4"-tert-butyltrityl)uridine 200 mmol of ribouridine are dissolved in 375 ml of anhydrous pyridine. The solution is heated to 60° C. and 220 mmol of solid uis-4,4',4"-tert-butyltrityl)chloromethane are added. After stirring for 6 hours at 60° C., the solvent is removed under vacuum and the residue is concentrated once from toluene and twice from acetonitrile. The crude product is dissolved in 600 ml of methyl chloride and washed with 200 ml of saturated bicarbonate solution. The organic phase is dried over Na$_2$SO$_4$ and the solvents are removed under vacuum. The residue is dissolved in 220 ml of a hot ethanol/water mixture (3:2) and crystallised at 0° C.

$^1$H-NMR (250 MHz, CDCl$_3$): 1.29 (s, c. 27H, 3 (CH$_3$) $_3$C-ar); 3.14 (br. d, 1H); 3.54 (ABM system, 2H, H$_2$C(5')); 4.18 (d-like m, 1H), 4.33 (m, 1H) and 4.45 (q-like m, 1H)(HC(2',3',4'); 5.23 (d, J=8, 1H, HC(5)); 5.35 (br. s, 1H); 5.91 (d, J=2, 1H, HC(1')); 7.15–7.35 (m, c. 12H,H-(ar)); 8.10 (d, J=8, 1H, HC(6)); 10.06 (br. s, HN(3)).

EXAMPLE C1

Preparation of 5'-(5'-(tris-4,4',4"-tert-butyltrityi) thymidine-3'-(S)-2,4-dichlorobenzylthioyl) thymidine-3'-(O)-cyanoethyl-(S)-2,4-dichlorobenzyl phosphorothioate 3.2 g of thymidine-3'-(S)-dichlorobenzyl(O)-cyanoethylphosphorothioate and 5.85 g of 5'-(Iris-4,4',4"-tert-butyltrityl)thymidine-3'-(O)-cyanoethyl-(S)2,4-dichlorobenzylphosphorothioate are dissolved in a solution of 4.25 ml of absolute N-methylimidazole and 8.1 g of triisopropylbenzenesulfonyl chloride in 125 ml of absolute pyridine. The mixture is stirred for 2.5 hours at room temperature and then 10 ml of water are added. The reaction mixture is concentrated to an oil at 55° C. The crude product is taken up in 500 ml of ethyl acetate and extracted in succession with 2×500 ml of aqueous N-methylmorpholinium hydrogencarbonate and once with 500 ml of brine. The organic phase is dried over sodium sulfate and, after removal of the salt, evaporated to dryness under vacuum at 55° C. The product is dissolved in ether and precipitated from petroleum ether. The precipitate is isolated by filtration and recrystallised from n-pentane, affording the title as a solid.

$^{31}$P-NMR (CDCl$_3$): 28.1, 27.8, 27.7, 27.3 (4-diastereoisomers); $^1$H-NMR (CDCl$_3$): 8.5–9 NH; 7.58: 1H, H$^6$; 7.26–7.4:16H, m, DCBn group, TTTr group, H$^6$; 6.44, 6.15: 2H, 2m, 1'; 5.05–5.2, 5.26–5.42: 2H, 2m, 3'; 4.05–4.45: 8H, m, DCBn group, CNE group, 5', 4', 3.3–3.5: 2H, m, 5'; 2.65–2.75, 2.38–2.6: 6H, CNE group, 2'; 1.84: 3H, s, CH$_3^5$; 1,3, s, 30 H, TTTr group, CH$_3^5$.

EXAMPLE C2

Use of 5'-(tris-4,4',4"-tert-butyltrityl)thymidine-3'-(cyanoethyl)phosphorodiisopropylamidite in the automatated DNA synthesis by the phosphite triester process The synthesis carried out with a commercially available DNA synthesizer (Applied Bio-systems Inc. (ABI)) with the reagents described by the manufacturer, i.e. acetonitrile, capping solution, oxidation solution, coupling reagent (tetrazole) and detritylation solution, CPG-DMTrT carrier. The synthesis protocol described by the manufacturer is carried out except for the detritylation time, which is doubled.

The following syntheses are performed: $T_{10}$, $T_{20}$ and $T_{30}$ are carried out with TTTr amiditc. As comparison, the sequence $T_{10}$ is carried out with known DMTr amidites using the same synthesis reagents. In all oligonucleotide syntheses, the 5'-terminal protective group, i.e. the TTrr group or, in the control sequence, the DMTr group, is left on the polymer after the last coupling step. When the synthesis is complete, the oligonucleotides are removed from the carrier with an aqueous saturated solution of ammonia at 55° C. over 15 hours. After filtering off the CPG carrier, the product solutions are lyophilised. The product mixtures are taken up in HPLC buffer, filtered, and separated over a commercial C-18 reversed phase column.

Analysis of the HPLC chromatgram shows that the TTTr amidites are just as suitable for the oligonucleotide synthesis by the phosphite triester process as the known DMTr amidites. The TTTr-terminally protected oligonucleotides have, under identical conditions, a higher retention on a C-18 reversed phase HPLC column, so that in the case of the TTTr group only a low order of column efficiency is necessary to separate the failure sequences.

What is claimed is:

1. A nucleoside, nucleoside analog, nucleotide, nucleotide analog or oligonucleotide from at least two up to 200 such identical or different nucleotides and/or nucleotide analogs that carry in the basic structure an unsubstituted or substituted residue of a nucleobase B and one primary protected hydroxyl group,
    said nucleoside, nucleoside analogue, nucleotide or nucleotide analogue comprising a carbocyclic, O- or S-heterocyclic structure,
    said nucleotide or nucleotide analogue further comprising a residue capable of forming an ester linking group selected from the group consisting of phosphorothioate, phosphorodithioate, phosphoroamidate, alkylphosphonate, hydrogenphosphonate, phosphate, carbonate and carbamate,
    wherein said unsubstituted or substituted residue of a nucleobase B is selected from the group consisting of adenine, N-methyladenine, N-benzoyladenine, 2-methylthioadenine, 2-aminoadenine, 2-hydroxypurine, 2-amino-6-chloropurine, 2-amino-6-methylthiopurine, guanine, N-isobutyrylguanine, uracil, thymine, cytosine, 5-fluorouracil, 5-chlorouracil, 5-bromouracil, dihydrouracil, 5-methylcytosine and their respective protected forms,
    said primary protected hydroxyl group being a 5'-hydroxy group protected by tris-4,4',4"-tert-butylphenylmethyl.

2. A nucleoside, nucleoside analog, nucleotide, nucleotide analog or oligonucleotide according to claim 1, wherein said nucleobase B is protected by a cycloalkylcarbonyl group which contains 3 to 12 ring carbon atoms and which is unsubstituted or substituted by $C_1$-$C_6$alkyl or $C_1$-$C_6$alkoxy, or by an amidine protective group.

3. A nucleoside, nucleoside analog, nucleotide, nucleotide analog or oligonucleotide according to claim 2, wherein the cycloalkylcarbonyl group contains 3 to 12 ring carbon atoms.

4. A nucleoside, nucleoside analog, nucleotide, nucleotide analog or oligonucleotide according to claim 3, wherein the cycloalkylcarbonyl group contains 5 or 6 ring carbon atoms.

5. A nucleoside, nucleoside analog, nucleotide, nucleotide analog or oligonucleotide according to claim 4, wherein the cycloalkylcarbonyl group is cyclohexanecarboxyl.

6. A nucleoside, nucleoside analog, nucleotide, nucleotide analog or oligonucleotide according to claim 1, which has one of the following formulae IIIa, IIIb, IIIc or IIId

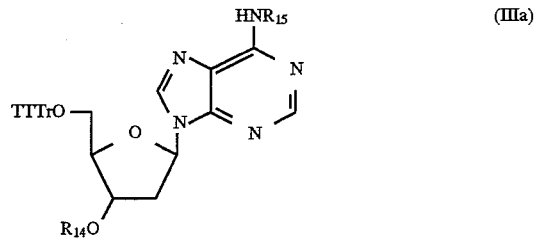

(IIIa)

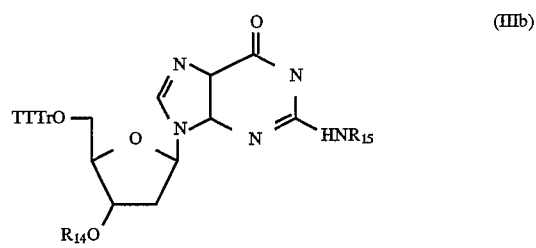

(IIIb)

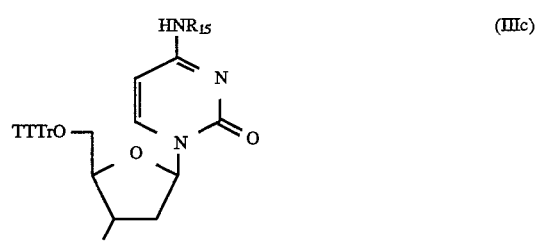

(IIIc)

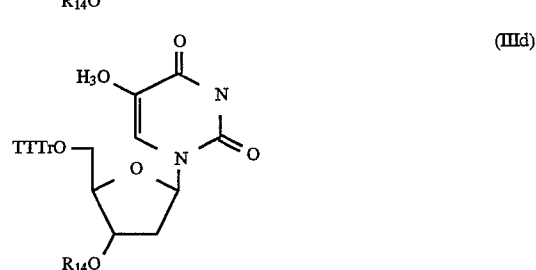

(IIId)

wherein $R_{14}$ is hydrogen or a radical which forms a nucleotide linking group and $R_{15}$ is hydrogen or cyclohexylcarbonyl.

7. A nucleoside, nucleoside analog, nucleotide, nucleotide analog or oligonucleotide according to claim 6, wherein $R_{14}$ is a phosphorus-containing radical of formula IVa, IVb or IVc

(IVa)

(IVb)

(IVc)

which forms a nucleotide linking group, wherein
Z is oxygen or sulfur;

X, X' and X" are each independently of one another oxygen or sulfur carrying a negative charge, with counterion Li, Na, K, Cs, tertiary or quartenary ammonium; or X' and X" are each independently of the other $C_1-C_{12}$alkyl, $C_6-C_{12}$aryl, $C_7-C_{20}$aralkyl, $C_7-C_{20}$alkaryl, —$OR_b$ or —$SR_b$;

X''' is $C_1-C_{12}$alkyl, $C_6-C_{12}$aryl, $C_7-C_{20}$aralkyl, $C_7-C_{20}$alkaryl, —$OR_b$ or —$SR_b$; and $R_b$ is $C_1-C_{12}$alkyl, $C_6-C_{12}$aryl, $C_7-C_{20}$aralkyl, $C_7-C_{20}$alkaryl;

$R_{18}$ and $R_{19}$ are each independently of the other hydrogen, $C_1-C_{12}$alkyl, $C_2-C_{12}$alkenyl, $C_6-C_{12}$aryl, $C_7-C_{20}$aralkyl or $C_7-C_{20}$alkaryl;

and alkyl, aryl, aralkyl and alkaryl in the definitions of $R_{18}$, $R_{19}$ and $R_b$ are unsubstituted or substituted by alkoxy, alkylthio, halogen, —CN, —$NO_2$, phenyl, nitrophenyl or halophenyl.

8. A process for the preparation of a nucleoside or nucleoside analog according to claim 1, which comprises reacting a nucleoside or nucleoside analog with tris-4,4',4"-tert-butyltrityl chloride in the presence of a sterically hindered tertiary amine in a suitable aprotic, polar, basic solvent.

9. A process for the preparation of an oligonucleotide of formula V

$$5'—OH(U)_m(V)_nOH-3' \qquad (v)$$

wherein U and V are identical or different, nucleoside residues or analogues thereof according to claim 1 and m and n are each independently of the other 0 or an integer from 1 to 200, and the sum of m and n is 2 to 200, by (a) reacting a compound of formula VI

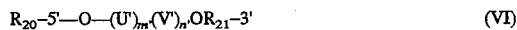
$$R_{20}-5'—O—(U')_{m'}(V')_{n'}OR_{21}-3' \qquad (VI)$$

wherein $R_{20}$ is a protective group and U' and V' have the meanings of U and V, m' and n' are each independently of the other 0 or an integer from 1 to 199, and the sum of m' and n' is 2 to 199, and $R_{21}$ is a phosphorus-containing radical of formula IVa, IVb or IVc

(IVa)

(IVb)

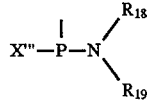
(IVc)

which forms a nucleotide linking group, wherein

Z is oxygen or sulfur;

X, X' and X" are each independently of one another oxygen or sulfur carrying a negative charge, with counterion Li, Na, K, Cs, tertiary or quartenary ammonium; or X' and X" are each independently of the other $C_1-C_{12}$alkyl, $C_6-C_{12}$aryl, $C_7-C_{20}$aralkyl, $C_7-C_{20}$alkaryl, —$OR_b$ or —$SR_b$;

X''' is $C_1-C_{12}$alkyl, $C_6-C_{12}$aryl, $C_7-C_{20}$aralkyl, $C_7-C_{20}$alkaryl, —$OR_b$ or —$SR_b$; and $R_b$ is $C_1-C_2$alkyl, $C_6-C_{12}$aryl, $C_7-C_{20}$aralkyl, $C_7-C_{20}$alkaryl;

$R_{18}$ and $R_{19}$ are each independently of the other hydrogen, $C_1-C_{12}$alkyl, $C_2-C_{12}$alkenyl, $C_6-C_{12}$aryl, $C_7-C_{20}$aralkyl or $C_7-C_{20}$alkaryl;

and alkyl, aryl, aralkyl and alkaryl in the definitions of $R_{18}$, $R_{19}$ and $R_b$ are unsubstituted or substituted by alkoxy, alkylthio, halogen, —CN, —$NO_2$, phenyl, nitrophenyl or halophenyl, with a compound of formula VII

$$5'—OH(U")_{m"}(V")_{n"}O—R_{22} \qquad (VII)$$

wherein U" and V" have the meanings of U and V, m" and n" are each independently of the other 0 or an integer from 1 to 198, and the sum of m" and n" is 2 to 198, and $R_{22}$ is (i) a radical of formula IVb, wherein Z is oxygen or sulfur; X' and X" are each independently of the other $C_1-C_{12}$alkyl, $C_6-C_{12}$aryl, $C_7-C_{20}$aralkyl, $C_7-C_{20}$alkaryl, —$OR_b$ or —$SR_b$; and $R_b$ is $C_1-C_{12}$alkyl, $C_6-C_2$aryl, $C_7-C_{20}$aralkyl, $C_7-C_{20}$alkaryl, and alkyl, aryl, aralkyl and alkaryl as defined for $R_b$ are unsubstituted or substituted by alkoxy, alkylthio, halogen, —CN, —$NO_2$, phenyl, nitrophenyl or halophenyl;

(ii) a hydroxyl protective group; or (iii) a linkage to a solid carrier material by means of a linking group;

(b) if necessary, repeating step (a) until an oligonucleotide of the desired length has formed, and, before each coupling, removing the protective group $R_{20}$, capping any free hydroxyl groups present, and then oxidising the resultant phosphite to the phosphate, (c) if desired, detaching or isolating the oligonucleotide, and (d) removing the residual protective group $R_{20}$, said protective group $R_{20}$ being TTTr.

10. A process according to claim 9, wherein the sum of m and n is 2 to 50.

11. A process according to claim 9, wherein the sum of m and n is 2 to 30.

12. A compound according to claim 2, wherein the amidine protective group is dimethylaminomethylidene.

* * * * *